US005807727A

United States Patent [19]
Uchida et al.

[11] Patent Number: 5,807,727
[45] Date of Patent: Sep. 15, 1998

[54] PECTINASE FROM *SACCHAROMYCES BAYANUS*

[75] Inventors: Setsuko Uchida; Satoshi Watabe, both of Yokohama, Japan

[73] Assignee: Japan Tobacco Inc., Tokyo, Japan

[21] Appl. No.: 458,870

[22] Filed: Jun. 2, 1995

Related U.S. Application Data

[62] Division of Ser. No. 5,148, Jan. 15, 1993, abandoned.

[30] Foreign Application Priority Data

| Jan. 20, 1992 | [JP] | Japan | 4-27436 |
| Dec. 3, 1992 | [JP] | Japan | 4-324160 |
| Dec. 3, 1992 | [JP] | Japan | 4-350022 |

[51] Int. Cl.$^6$ ............... C12N 9/26; C12N 1/16
[52] U.S. Cl. ............ 435/201; 435/254.1
[58] Field of Search .......... 435/201, 254.21, 435/71.1

[56] References Cited

U.S. PATENT DOCUMENTS

| 4,605,622 | 8/1986 | Hasegawa et al. | 435/182 |
| 4,672,034 | 6/1987 | Rombouts et al. | 435/101 |
| 4,686,187 | 8/1987 | Sakai et al. | 435/275 |
| 4,689,322 | 8/1987 | Kulbe et al. | 514/54 |
| 4,820,520 | 4/1989 | Yokosuka et al. | 424/439 |
| 4,871,544 | 10/1989 | Eckenhoff | 424/438 |
| 4,873,095 | 10/1989 | Rundle | 426/50 |
| 5,008,254 | 4/1991 | Weibel et al. | 514/57 |
| 5,099,009 | 3/1992 | Thibault et al. | 536/2 |
| 5,275,834 | 1/1994 | Thibault et al. | 426/577 |

FOREIGN PATENT DOCUMENTS

| 249764 | 12/1987 | European Pat. Off. . |
| 552728 | 7/1993 | European Pat. Off. . |
| 57-083286 | 5/1982 | Japan . |
| 57-163477 | 10/1982 | Japan . |
| 57-163478 | 10/1982 | Japan . |
| 59-71699 | 4/1984 | Japan . |
| 2-2330 | 1/1989 | Japan . |
| 2-72853 | 3/1989 | Japan . |
| 2-97396 | 4/1990 | Japan . |
| 495368 | 11/1989 | U.S.S.R. . |

OTHER PUBLICATIONS

H.P. Call et al., Screening for Pectinolytic Candida Yeasts: Optimization and Characterization of the Enzymes, *Journal of Food Biochemistry.*, vol. 9, pp. 193–210, 1988.

P. N. Shastri et al., Production, Purification and Properties of *Geotrichum candidum* Polygalacturonas: Regulation of Product by Pyruvate, *Indian Journal of Biochemistry & Biophysics*, vol. 25, pp. 331–335, Aug. 1988.

P. Dechau et al., Degradation of Pectin Compounds by Yeasts of the Genus Saccharomyces, CA79(9):51808h.

Wimborne et al. (1978) Biotechnol. Bioeng., vol. XX, "Pectinolytic Activiy of *Saccharomyces fragilis* Cultured in Controlled Environments", pp. 231–242.

"Enzymic Degradation of Pectic Acid" C. Hatanaka et al, *Ber. Ohara. Inst. Landwirtsch. Biol.* 14, 189 (1969).

"Enzymic Degradation of Isolated Pectic Substances and Cell Wall from Pulp of Grape Berries", L. Sauliner et al, *Carbohydrate Polymers*, 7, 345 (1987).

"Properties of Yeast Polygalacturonase", B. S. Luh et al, *Arch. Biochem. Biophys.* 48, 23 (1954).

"End Products and Mechanism of Hydrolysis of Pectin and Pectic Acid by Yeast Polygalacturonase (YPG)" B.S. Luh et al, *Arch. Biochem. Biophys.*, 51, 102 (1954).

"Pectin–Polygalacturonase of *Saccharomyces fragilis*", J. Ozawa et al, *Nogaku Kenkyu (Agricultural Studies)*, 47, 105 (1959).

"The Active Site of Yeast Endo–Polygalacturonase Contains Seven Subsites", J.H. McClendon, *Phytochemistry*, 18, 765 (1979).

"Multiple Forms of Endo–Polygalacturonase from *Saccharomyces fragilis*", Jaiyun Lim et al, *Agric. Biol. Chem.*,44 (3), 473 (1980).

"Production, Purification and Properties of *Geotrichrum candidum* Polygalacturonase: Regulation of Production by Pyruvate", P. N. Shastri et al, *Indian Journal of Biochemistry & Biophysics*, 25, 331 (1988).

"Screening for Pectinolytic Candida Yeasts: Optimization and Characterization of the Enzymes", H.P. Call et al, *J. Food Biochem.*, 9 (3), 193 (1985).

"Maceration Activity of an Endopolygalacturonase from *Candida macedoniensis*", H. P. Call et al, *J. Food Biochem.*, 9 (4), 325 (1985).

"Isolation of a Pectin–Utilizing Yeast from Cocoa Beans", R. Ravelomanana, CA106 (11):81303h.

"Peptidase and Plygalacturonase Activity of Brewer's Yeasts *Saccharomycetaceae carlsbergensis* Strain 11", S. Abdurazakova, CA79 (21):124679d.

"Effect of Glucose and Other Carbon Sources on Accumulation of Polygalacturonase by the Yeast *Saccharomyces pastorianus*", N. Astapovich, CA114(7):58681m.

"Comparative Study of Yeast Hydrolase Activity", S. Abdurazakova et al, CA110 (11):93481k.

(List continued on next page.)

*Primary Examiner*—Jon P. Weber
*Attorney, Agent, or Firm*—Birch, Stewart, Kolasch & Birch, LLP

[57] ABSTRACT

A pectinase for degradation a pectin or pectic acid is disclosed wherein (1) the novel pectinase is an endopolygalacturonase produced from a, *Saccharomyces bayanus*,
(2) the optimal pH is 4.0,
(3) the stable pH range is 4.0 to 8.0,
(4) the optimal temperature is 45° C.,
(5) the enzymatic activity is stable up to 45° C., and
(6) the molecular weight is 38,000. A low-molecular pectin having a low viscosity and a high solubility and maintaining the physiological activity as the dietary fiber, and food and drink each of which contains 0.01 to 50 wt % of the low molecular pectin are also disclosed.

2 Claims, 3 Drawing Sheets

OTHER PUBLICATIONS

"Pectinolytic Activities from Lactose and Lactic Acid Assimilating Yeasts. II. Characterization of Pectinolytic Enzymes", H. Call, *CA*89 (17):142987p.

"Polygalacturonase and Pectin Esterase Function of Some Yeasts of the genus Saccharomyces", S. Maksimova et al, *CA*86 (19):137932a.

Sanchez et al. "A Study of the Polygalacturonase Activity of Several Yeast Strains Isolated from Coca", *Applied Microbiology and Biotechnology*, vol. 20, No. 4, 1984, pp. 262–267.

*Agric. Biol. Chem.*, 48 (3), pp. 633–640, 1984, Inoue et al.

"The Impairment of Cloud Stability of Orangeade by Yeasts", W. Roecken et al, *Zeitschrift fur Lebensmittel–Untersiuchung Und–Forschung*, vol. 173, No. 1, 1981, pp. 26–31.

"Utilization of Endopolygalacturonase from Kluyveromyces–Fragilis in the Clarification of Apple Juice", L. Gomez–Ruiz et al, *Journal of Food Science*, vol. 53, No. 4, 1988, pp. 1236–1237.

"Large–Scale Preparation of Galacturonic Acid Oligomers by Matrix–Bound Polygalacturonase", Houdenhoven et al, *Amsterdam NL*, vol. 34, No. 2, 1974, pp. 233–239.

Fellows et al. (1984) *Enz. Micrombiol. Technol*, 6(9), "An Investigation into the Pectolytic Activity of the Yeast *Sacchcharomycopsis fibular*", pp. 405–410.

Blanco et al. (1994) *Can. J. Micorobiol.*, 40(1), "Production and Partial Characterization of an Endopol;ygalacturonase from *Saccharomyces cerevisiae*", pp. 974–977.

Luh et al. (1951) *Arch. Biochem. Biophys.*, 33, "Studies on Polygalacturonase of Certain Yeasts", pp. 212–227.

Inoue et al. (984) *Agric. Biol. Chem.*, 48(3), "Preparation of Cross–Linked Pectate and its Application to the Purification of Endopolygalacturonase of *Kluyveromyces fragilis*", pp. 633–640.

Sanchez et al. (1984) *Appl. Microbiol. Biotechnol.*, 20(4), "A Study of the Polygalactunoase Activity of Sevaral Yeast Strains Isolated from Cocoa", pp. 262–267.

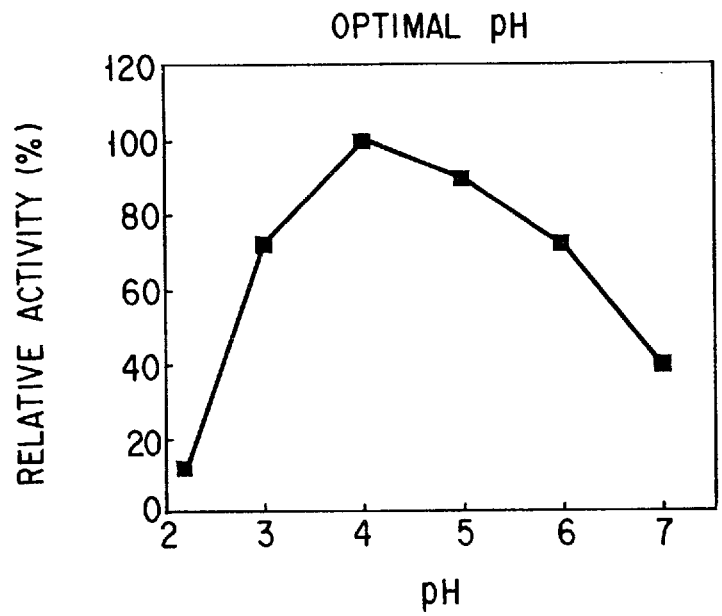
F I G. 1
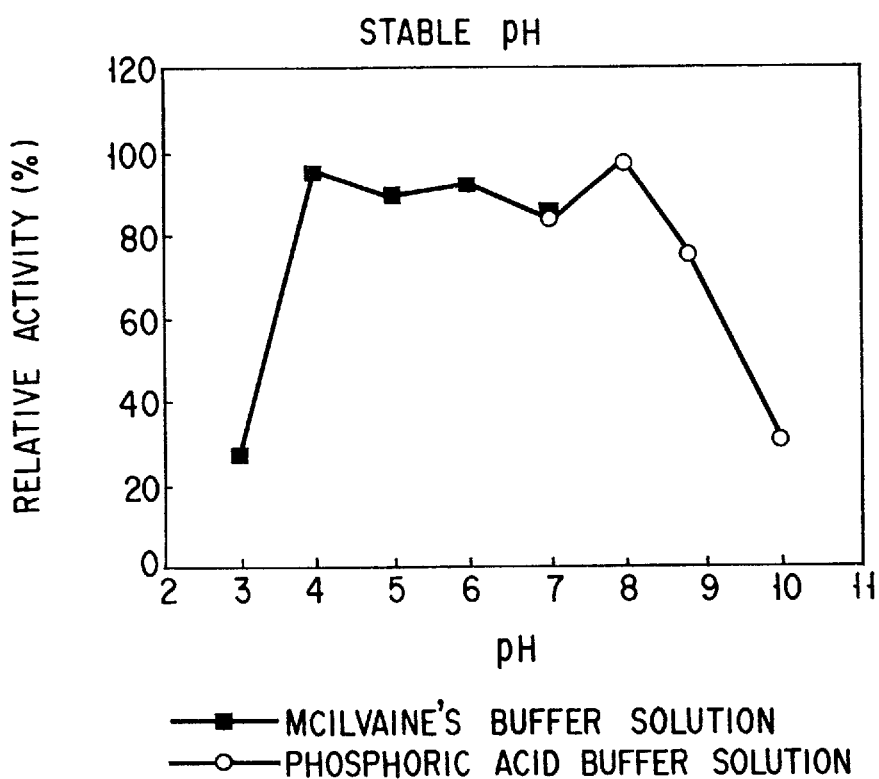
F I G. 2

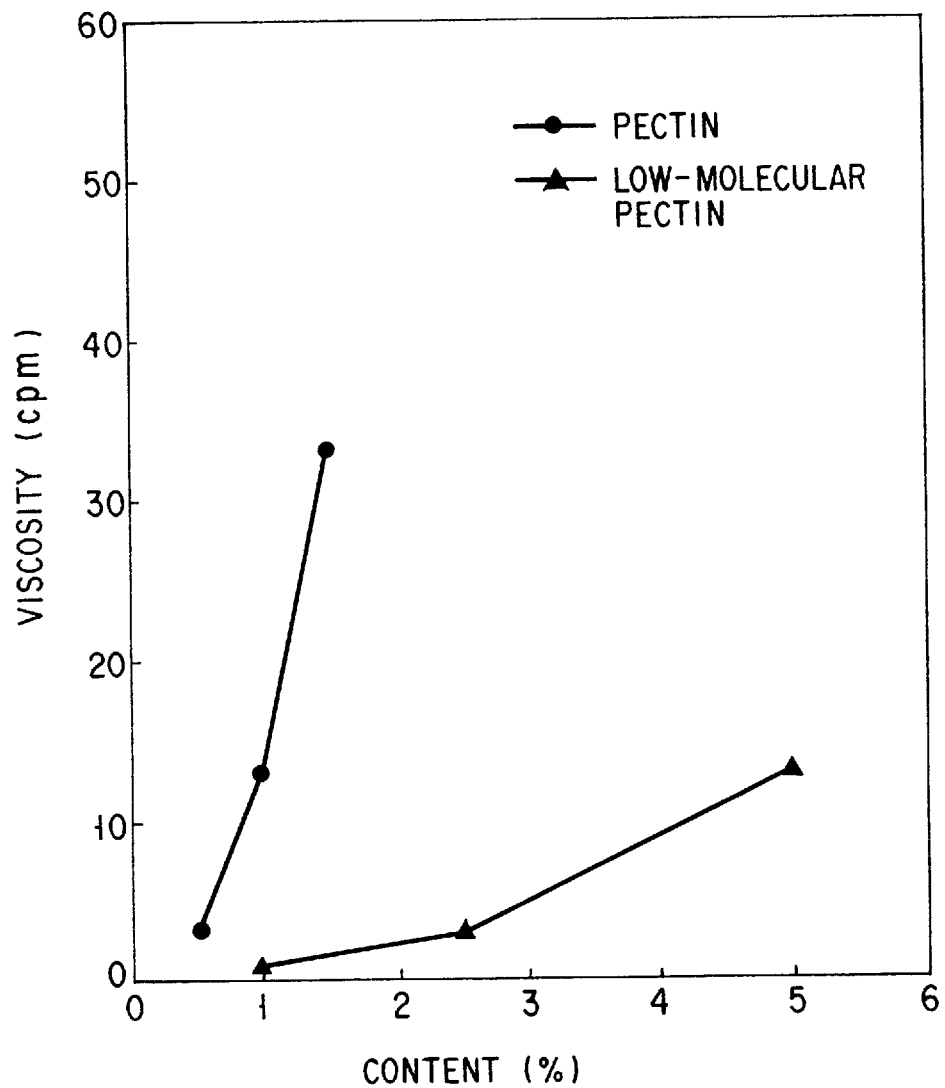
F I G. 5

PECTINASE FROM SACCHAROMYCES BAYANUS

This application is a divisional application Ser. No. 08/005,148, filed on Jan. 15, 1993, now abandoned, the entire contents of which are hereby incorporated by reference.

BACKGROUND OF THE INVENTION

1. Field of the Invention

The present invention relates to a novel pectinase capable of degrading a pectin into a low-molecular pectin having a molecular weight of 20,000 to 80,000. The present invention also relates to a low-molecular pectin converted from a pectin while the physiological activity of the pectin as a dietary fiber is maintained, and food and drink which contain the low-molecular pectin.

2. Description of the Related Art

Dietary fibers are defined as hard digestive components in foodstuffs which cannot be digested by human digestive enzymes. The dietary fibers include non-digestive organic materials such as chitin and chitosan in addition to plant cell wall components such as cellulose, lignin, and pectin. In recent years, these dietary fibers are found to have various activities such as a defecation improving effect and an activity of reducing the cholesterol content of blood and to play an important role in preventing diseases of adult people.

Of these dietary fibers, pectic substances such as a pectin and pectic acid have a strong activity as the dietary fibers. Various effects such as a defecation improving effect, an effect of repressing the level of the cholesterol content of blood, an effect of repressing formation of gallstones, and a hypertensive repression effect have been reported. Conventionally, pectic substances have been used as stabilizers in jams, fruit jellies, yoghurt drinks, and lactic acid beverages in food industries. Since the pectic substances have the above effects, they are expected as dietary fibers to be added in food and drink.

A pectic substance is bound with the cellulose in an unripe fruit or plant to be present in the form of a complex called a protopectin. In particular, the protopectin is contained in citrus fruits, apples, and chinese quinces in large amounts. Although this protopectin is insoluble, it is hydrolyzed to produce a soluble pectin or pectic acid when the fruit is ripened.

Of these products, the pectin is a polysaccharide containing galacturonane as a polymer of galacturonic acid as a major component and small amounts of rhamnose, arabinose, xylose, and galactose and having a molecular weigh of 200,000 or more.

The pectin generally has a low solubility and a high viscosity and tends to gel. For this reason, although the pectin has the various effects as described above, only a small amount of pectin is added to food and drink, and it is difficult to add the pectin in food and drink in an amount enough to expect the activity of the dietary fiber.

SUMMARY OF THE INVENTION

It is, therefore, the first object of the present invention to provide a low-molecular pectin which has a high solubility and a low viscosity and maintains the physiological activity as the dietary fiber.

It is the second object of the present invention to provide food and drink which contain the low-molecular pectin.

It is the third object of the present invention to provide a novel pectinase useful for preparing the low-molecular pectin.

In order to achieve the above objects of the present invention, a pectin is degraded using a pectinase to obtain a low-molecular pectin which has a low viscosity and a high solubility. The present inventors made extensive studies on many pectinase on the basis of the above assumption. As a result, the present inventors found that endopolygalacturonases (EC3. 2. 1. 15) derived from a yeast (i.e., *Kluyveromyces fragilis,* JTF-1) belonging to the genus Kluyveromyces, a yeast (i.e., *Geotrichum candidum,* JTF-2) belonging to the genus Geotrichum, a yeast (i.e., *Candida Kefyr,* JTF-3) belonging to the genus Candida, and a yeast (i.e., *Saccharomyces bayanus,* JTF-4) belonging to the genus Saccharomyces were suitable as pectinase. In addition, the present inventors also found that even if enzymes obtained from the above yeasts were caused to act up to the degradation limit, the decrease in molecular weight of the pectin by degradation was stopped at the molecular weight of about 20,000, and degradation no longer progressed. The present inventors also found that low-molecular pectins having molecular weights of 20,000 to 80,000 could be obtained by appropriate reaction condition control.

The present inventors have deposited the microorganisms for producing the pectinase (endopolygalacturonases) used in the present invention designated as JTF-1 (accession number: FERM BP-4056) on Oct. 11, 1991, JTF-2 (accession number: FERM BP-4057) on Dec. 19, 1991, JTF-3 (accession number: FERM BP-4058) on Mar. 6, 1992, and JTF-4 (accession number: FERM BP-3916) on Jul. 9, 1992 with the Fermentation Research Institute, Agency of Industrial Science and Technology located at 1-3, Higashi 1-chome, Tukuba-shi, Ibaraki-ken 305, Japan in accordance with the Budapest Treaty on the International Recognition of the Deposit of Microorganisms for the Purposes of Patent Procedures.

The present inventors found for the first time that JTF-4 produced an endopolygalacturonase.

According to the first aspect of the present invention, therefore, there is provided a novel pectinase having the following natures (i) to (vi).

(i) A novel pectinase is an endopolygalacturonase which is produced from the genus Saccharomyces and degrades the pectin and the pectic acid.

(ii) An optimal pH upon reaction at 35° C. for 20 minutes is 4.0.

(iii) A stable pH range upon heating at 35° C. for 60 minutes is 4.0 to 8.0.

(iv) An optimal temperature upon reaction at a pH of 5.0 is 45° C.

(v) The enzymatic activity upon heating at a pH of 5.0 for 60 minutes is stable up to 45° C.

(vi) The molecular weight is 38,000.

According to the second aspect of the present invention, the endopolygalacturonases (the endopolygalacturonases produced from the yeasts JTF-1 to JTF-4 will be referred to as JTFP-1, JTFP-2, JTFP-3, and JTFP-4, respectively) produced from JTF-1, JTF-2, JTF-3, and JTF-4 are caused to act on pectins to obtain low-molecular pectins.

According to the third aspect of the present invention, there are provided food and drink which contain 0.01 to 50 wt % of the low-molecular pectin.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

FIG. 1 is a graph showing the relative activity and the pH to determine an optimal pH of an enzyme (JTFP-4);

FIG. 2 is a graph showing the relative activity and the pH to determine a stable pH range of the enzyme (JTFP-4);

FIG. 5 is a graph showing a viscosity curve of a low-molecular pectin according to the present invention.

DETAILED DESCRIPTION OF THE PREFERRED EMBODIMENT

Figure 3:
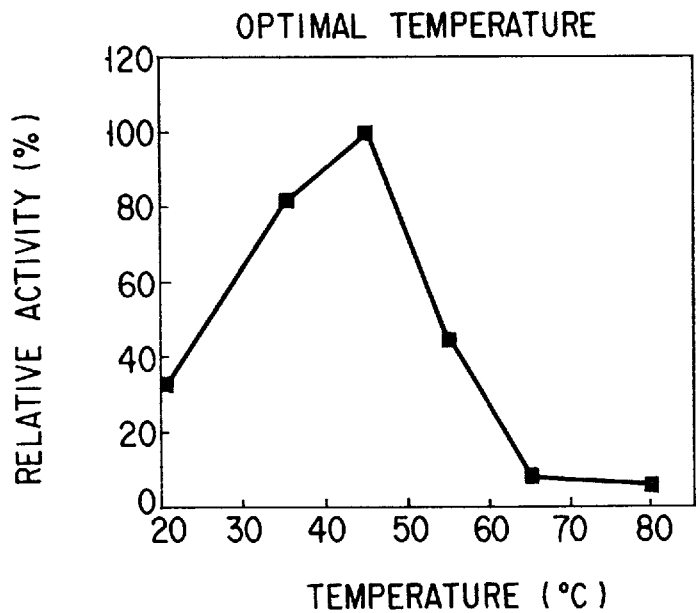
FIG. 3 is a graph showing the relative activity and the temperature to determine an optimal temperature of the enzyme (JTFP-4)

The present invention will be described in detail below.

An endopolygalacturonase (JTFP-4) derived from JTF-4 belonging the genus Saccharomyces according to the present invention will be described below.

JTFP-4 as the enzyme of the present invention acts on a pectin and pectic acid to hydrolyze them. JTFP-4 has the following physicochemical properties.

(1) Substrate Specificity

JTFP-4 according to the present invention degrades the pectin and pectic acid, but does not degrade soluble starch, dextrin, and xylan.

(2) Optimal pH

JTFP-4 according to the present invention has an optimal pH near a pH of 4.

(3) Stable pH Range

JTFP-4 according to the present invention is stable in the pH range of 4 to 8.

(4) Enzymatic Activity

The enzymatic activity of JTFP-4 is 33.9 units/mg protein (1 unit: an amount of enzyme for producing 1 $\mu$mol of a reducing group of the hydrolysate per minute at 35° C. in the hydrolysis of pectic acid).

(5) Optimal Temperature

JTFP-4 according to the present invention has an optimal temperature near 45° C.

(6) Stable Temperature

JTFP-4 according to the present invention is stable until 45° C.

(7) Influence of Metal Ion and Inhibitor

JTFP-4 according to the present invention is inhibited by 69% with barium chloride, but is not inhibited with magnesium sulfate.

(8) Molecular Weight

The molecular weight of JTFP-4 is 38,000.

(9) Amino Acid Composition

JTFP-4 according to the present invention has a maximum content of glutamine and glutamic acid in a molecule (130 residues per molecule).

According to the present invention, the endopolygalacturonase is caused to act on the pectin to obtain a low-molecular pectin.

The endopolygalacturonases generally exist in bacteria, yeasts, fungi, and higher plants. Many steps are required to purify the enzyme from these sources. That is, cells are removed from a culture solution containing microorganisms or the like to obtain a culture supernatant. The culture supernatant is subjected to ammonium sulfate precipitation to salt out only a protein. The protein is separated based on charges thereof using an ion exchange material. The enzyme is separated by gel filtration in accordance with molecular weights, thus purifying the endopolygalacturonase in accordance with such a general enzyme purification process.

According to the present invention, when a commercially available pectinase is used, purification must be performed to eliminate pectin esterase and hemicellulase from the pectinase.

Since JTFP-1, JTFP-2, JTFP-3, and JTFP-4 produced from JTF-1, JTF-2, JTF-3, and JTF-4, respectively, are extracellular enzymes secreted outside the microorganisms, the culture supernatant can be directly used as a crude enzyme solution. The culture supernatant can be generally obtained such that the yeast is cultured on an agar slant and is then cultured in mass production. The resultant cultured product is centrifuged to eliminate the microorganisms. In this manner, the culture supernatant obtained using the yeast can be directly used in an enzymatic reaction, thereby advantageously simplifying the enzyme purification process.

The culture supernatant is preferably subjected to a simple treatment such as dialysis, ultrafiltration, ion exchange, or gel filtration to eliminate the yeast smell produced in the reaction using this enzyme and to obtain a more transparent solution.

A low-molecular pectin is obtained such that the purified product, culture supernatant, or its treated product of the endopolygalacturonase obtained as described above is reacted with a suspension obtained by suspending a pectin in a buffer solution such as acetic acid.

The type of endopolygalacturonase used in the present invention is not limited to a specific one if it reacts with a pectin to produce a low-molecular pectin having a molecular weight of about 20,000 to 80,000. However, JTFP-1 to JTFP-4 free from laborious operations such as enzymatic purification are preferably used.

As a pectin used in the present invention, any pectin material can be used, and its origin is not limited to a specific one. Therefore, generally known pectins originating from fruits, such as a lemon pectin and an apple pectin can be used.

In a reaction between the pectin and one of JTFP-1 to JTFP-4, a purified product, a culture supernatant (crude enzyme solution), or its treated product may be used to react with the pectin.

The degradation reaction by the enzyme is preferably performed for a reaction time of 12 to 48 hours when the content of the yeast culture supernatant is 5 to 20 parts by weight with respect to 1 part by weight of the pectin. The preferable reaction temperature and pH are those which allow a sufficient reaction and do not inactivate the endopolygalacturonase, i.e., 30° to 50° C. and a pH of 4.0 to 8.0.

According to the present invention, even if the enzymatic reaction is performed at the degradation limit, the degradation of the pectin is stopped when its molecular weight is about 20,000. Therefore, by controlling the reaction conditions such as the reaction time, a low-molecular pectin having an arbitrary molecular weight falling within the range of about 20,000 to 80,000 can be obtained.

Although the low-molecular pectin according to the present invention can have a molecular weight of about 20,000 to 80,000, the molecular weight preferably falls within the range of about 50,000 to 70,000 in view of retention of the physiological activity as the dietary fiber and ease in addition of the low-molecular pectin in food and drink. A low-molecular pectin most preferably has a molecular weight of about 60,000.

The degraded product of the pectin may be directly dried and used, or may be further treated.

When a further treatment is to be performed, the degraded product of the pectin is purified by dialysis or ultrafiltration to eliminate galacturonic acid and its oligosaccharide in the degraded product and acetic acid used as the buffer solution in the reaction. The purified degraded product is precipitated using an organic solvent such as ethanol or acetone or dried by freeze drying or spray drying to obtain a powder for later applications.

According to the present invention, there are provided food and drink which contain low-molecular pectins of the present invention.

The low-molecular pectin obtained by the above method according to the present invention has a molecular weight falling within the range from that of a polysaccharide such as pectin or agarose to that of an oligosaccharide such as maltooligosaccharide or fructooligosaccharide. Although the low-molecular pectin has a lower viscosity and a higher solubility than those of the original pectin, it has a defecation improving effect as one of the physiological activities of the dietary fiber.

On the other hand, since the low-molecular pectin according to the present invention has the above properties, it can be contained in an amount which allows to maintain the physiological activity as the dietary fiber, i.e., 0.01 to 50 wt %, and preferably 0.1 to 5 wt %, which cannot be conventionally contained, in a variety of food and drink such as juices, candies, breads, and jams.

The food and drink which contain low-molecular pectins according to the present invention exhibit improved physical properties and an improved palate at the above contents. These physical properties and palate are different from those obtained in a case wherein a conventional pectin is added to food and drink.

As described above, since the enzymes (JTFP-1 to JTFP-4) used in the present invention are extracellular enzymes secreted outside the microorganisms, the culture supernatant can be directly used as a crude enzyme solution and in the enzymatic reaction. Therefore, the enzyme can advantageously simplify the enzyme purification process and easily degraded the pectin into a low-molecular pectin. When the enzymes used in the present invention are caused to act on pectins up to the degradation limit, the decrease in molecular weight of the pectin upon degradation can be stopped at about 20,000, and further degradation cannot progress according to the characteristic feature of the enzyme. By controlling the reaction conditions, a low-molecular pectin having a molecular weight falling within the range of about 20,000 to 80,000 can be obtained.

Since the resultant low-molecular pectin has a low viscosity and a high solubility and can maintain the physiological activity (e.g., a defecation improving effect) of the dietary fiber, the low-molecular pectin can be easily added in the food and drink in an amount enough to provide the physiological activity as the dietary fiber.

The present invention will be described by way of its examples, but is not limited thereto.

[EXAMPLES]

Parts and percentage represent parts by weight and wt % throughout the examples, unless otherwise specified.

Example 1

Method of Culturing JTF-1 to JTF-4 and Preparation of Crude Enzyme Solutions (1) Method of Culturing JTF-1 and Preparation of Crude Enzyme Solution

*Kluyveromyces fragilis* JTF-1 was cultured on the slant of potato sucrose agar (pH of 5.0) at 27° C. for 24 hours. The cultured *Kluyveromyces fragilis* in one platinum loop was inoculated in 50 ml of a medium (pH of 5.0) containing 5% of glucose, 0.2% of ammonium phosphate, 0.1% of potassium primary phosphate, 0.1% of magnesium sulfate, and 0.4% of a yeast extract and was stationarily cultured at 27° C. for 3 days. This cultured product was inoculated in 1 l of a medium having the same composition as above the culture medium and was stationarily cultured at 27° C. for 3 days. The resultant cultured product was centrifuged at 13,000 rpm for 10 minutes to eliminate JTF-1, thereby obtaining a culture supernatant.

(2) Method of Culturing JTF-2 and Preparation of Crude Enzyme Solution

A culture supernatant was obtained following the same procedures as in (1) except that *Geotrichum candidum* JTF-2 was used in place of *Kluyveromyces fragilis* JTF-1.

(3) Method of Culturing JTF-3 and Preparation of Crude Enzyme Solution

*Candida Kefyr* JTF-3 was cultured on the slant of potato sucrose agar (pH of 5.0) at 22° C. for 3 days. The cultured *Candida Kefyr* in one platinum loop was inoculated in 50 ml of a medium (pH of 5.0) containing 5% of glucose, 0.2% of ammonium phosphate, 0.1% of potassium primary phosphate, 0.1% of magnesium sulfate, and 0.4% of a yeast extract and was stationarily cultured at 22° C. for 3 days. This cultured product was inoculated in 1 l of a medium having the same composition as the above culture medium and was stationarily cultured at 22° C. for 4 days. The resultant cultured product was centrifuged at 8,000 rpm for 10 minutes to eliminate JTF-3, thereby obtaining a culture supernatant.

(4) Method of Culturing JTF-4 and Preparation of Crude Enzyme Solution

*Saccharomyces bayanus* JTF-4 was cultured on the slant of potato sucrose agar (pH of 5.0) at 28° C. for 3 days. The cultured *Saccharomyces bayanus* in one platinum loop was inoculated in 50 ml of a liquid medium (5% of glucose, 0.2% of ammonium phosphate, 0.1% of potassium primary phosphate, 0.1% of magnesium sulfate, and 0.4% of a yeast extract; pH of 5.0) contained in a 200-ml Erlenmeyer flask and was stationarily cultured at 28° C. for 3 days. This cultured product was inoculated in 1 l of a medium having the same composition as the above culture medium and contained in a 3-l Erlenmeyer flask and was stationarily cultured at 28° C. for 3 days. The resultant cultured product was centrifuged at 8,000 rpm for 10 minutes to eliminate JTF-4, thereby obtaining a culture supernatant.

Example 2

Method of Preparing JTFP-4

The culture supernatant obtained in Example 1 was filtered through a millipore filter (pore size: 0.45 μm) to perfectly eliminate JTF-4. The culture filtrate was dialyzed overnight in a 0.02 M acetic acid buffer solution (pH of 5.0) at 5° C. About 600 ml of the dialyzed culture supernatant were adsorbed in an ion exchange column (S-Sepharose)

and were eluted in accordance with a density gradient method using an aqueous sodium chloride solution. Active fractions were collected, and gel filtration column chromatography (Sephadex G-75) was performed using a 0.02 M acetic acid buffer solution as an eluent. This chromatogram exhibited one highly active peak. The fractions corresponding to the highly active peak were collected and dialyzed overnight in distilled water at 5° C. The dialyzed product was condensed to 5 ml by gel filtration. About 1 mg of a purified enzyme was obtained as a protein from 600 ml of the culture supernatant.

The enzymatic activity (one unit) was determined by measuring the number of reducing groups in the hydrolysate obtained by the enzymatic reaction in accordance with the Somogyi-Nelson method. That is, one unit is an amount of enzyme for producing 1 $\mu$mol of the reducing groups of the hydrolysate per minute at 35° C. (the number of produced reducing groups is figured out as an amount of galacturonic acid). As a result of this measurement, the enzymatic activity according to the present invention was found to be 33.9 units/mg protein.

When SDS polyacrylamide electrophoresis was performed using this sample, the sample was detected as a single band.

Example 3

The following experiment was performed to examine the properties of the enzyme (JTFP-4) of the present invention.

(1) Substrate Specificity

In order to examine the substrate specificity of the enzyme, reactivity between the enzyme and substrates shown in Table 1 was examined.

Each substrate was added so that the final concentration of a 0.2M acetic acid buffer solution (pH of 5.0) was set to be 0.2%. 0.1 ml of an enzyme solution was added to 0.15 ml of each resultant solution and was reacted therewith at 35° C. for 20 minutes. The presence/absence of the substrate degradation activity was detected by measuring the number of reducing terminals for each substrate. The degradation activity for each substrate is shown in Table 1. A mark o in Table 1 represents a substrate degraded by the enzyme, and a mark x represents a substrate not degraded by the enzyme.

TABLE 1

Substrate Specificity

| Substrate | Degradation |
|---|---|
| Pectin | o |
| Pectic acid | o |
| Dextrin | x |
| Starch | x |
| Xylan | x |

As is apparent from Table 1, the enzyme of the present invention can degrade the pectin and pectic acid, but does not degrade a soluble starch, dextrin, and xylan.

(2) Optimal pH 0.02 ml of an enzyme solution were added to 0.23 ml of a McIlvaine buffer solution having a pH of 2 to 7 and containing pectic acid to obtain a final concentration of 0.2% and were reacted therewith at 35° C. for 20 minutes. The activity was measured by a Somogyi-Nelson method. Enzymatic activity values were measured as relative activities when the maximum activity value was defined as 100%. As shown in FIG. 1, the relative activities obtained by the Somogyi-Nelson method were plotted as a function of the pH to obtain an optimal pH. As is apparent from FIG. 1, the optimal pH of the enzyme of the present invention was near 4.

(3) Stable pH Range

Buffer solutions were a 0.2M McIlvaine buffer solution (pH of 3 to 7) and a phosphoric acid buffer solution (pH of 7 to 10).

0.025 ml of the enzyme of the present invention were added to 0.125 ml of each buffer solution having a pH of 3 to 10 and were treated at 35° C. for an hour. 0.15 ml of a 0.5 M acetic acid buffer solution (pH of 5.0) were added to the treated solution to adjust the pH to 5.0. Pectic acid was added to this solution so that the final concentration was adjusted to 0.2%, the resultant solution was reacted at 35° C. for 20 minutes, and the activity was measured by the Somogyi-Nelson method. Enzymatic activity values were measured as relative activities when the maximum activity value was defined as 100%. As shown in FIG. 2, the relative activities obtained by the Somogyi-Nelson method were plotted as a function of the pH to obtain a stable pH range. As is apparent from FIG. 2, the enzyme of the present invention was stable within a pH range of 4 to 8.

(4) Optimal Temperature 0.02 ml of the enzyme of the present invention were added to 0.23 ml of a 0.2M McIlvaine buffer solution (pH of 5.0) containing 0.2% of pectic acid and were reacted therewith at a temperature of 20° C. to 80° C. for 5 minutes, and the activity was measured by the Somogyi-Nelson method. Enzymatic activity values were measured as relative activities when the maximum activity value was defined as 100%. As shown in FIG. 3, the relative activities obtained by the Somogyi-Nelson method were plotted as a function of the temperature to obtain an optimal temperature. As is apparent from FIG. 3, the optimal temperature of the enzyme of the present invention was about 45° C.

Figure 4:
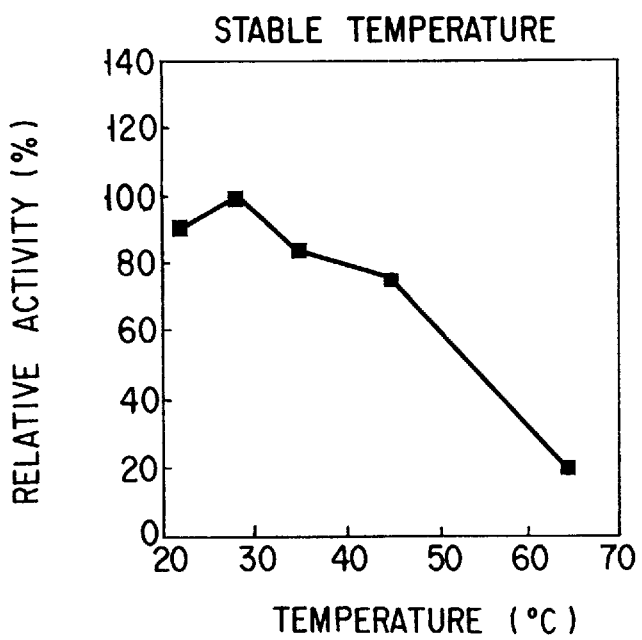
FIG. 4 is a graph showing the relative activity and the temperature to determine a stable temperature range of the enzyme (JTFP-4)

(5) Stable Temperature Range 0.02 ml of the enzyme of the present invention were added to 0.13 ml of a 0.5M McIlvaine buffer solution (pH of 5.0) and were heat-treated at a temperature of 20° C. to 65° C. for 60 minutes. After the reaction solution was cooled with ice, 0.1 ml of a 0.5% aqueous pectic acid solution was added to each treated solution and was reacted therewith at 35° C. for 20 minutes, and the activity was measured by the Somogyi-Nelson method. Enzymatic activity values were measured as relative activities when the maximum activity value was defined as 100%. As shown in FIG. 4, the relative activities obtained by the Somogyi-Nelson method were plotted as a function of the temperature to obtain a stable temperature range. As is apparent from FIG. 4, the relative activity of the enzyme of the present invention was 73% up to 45° C., but was reduced to about 20% at 65° C. The stable temperature range of this enzyme was limited up to 45° C.

(6) Influence of Metal Ion and Inhibitor

Influences of a metal ion and an inhibitor on the enzyme of the present invention were examined.

Each metal ion and the inhibitor in Table 2 were added in 0.15 ml of a 0.2 M acetic acid buffer solution (pH of 5.0) containing 0.002 ml of the purified enzyme solution to obtain a concentration of 1 mM. Each solution was reacted at 35° C. for 5 minutes, and 0.1 ml of a 0.5% aqueous pectic acid solution was added thereto. The resultant solution was reacted at 35° C. for 20 minutes, and an inhibition ratio was calculated using the Somogyi-Nelson method. Results are shown in Table 2. The inhibition ratio is a relative value with reference to a case (0%) in which a metal or inhibitor is not added.

TABLE 2

Influence of Metal and Inhibitor

| Compound | Concentration (mM) | Inhibition Ratio (%) |
|---|---|---|
| No additive | — | 0 |
| $BaCl_2$ | 1 | 69 |
| KCl | 1 | 35 |
| $Pb(CH_3COO)_2$ | 1 | 54 |
| $MgSO_4$ | 1 | 0 |
| $FeSO_4$ | 1 | 18 |
| $CaCl_2$ | 1 | 31 |

As is apparent from Table 2, the enzyme was inhibited by a barium ion (barium chloride) by 69%. No inhibition was found with a magnesium ion (magnesium sulfate).

(7) Molecular weight

The molecular weight of this enzyme obtained in Example 2 was measured by SDS polyacrylamide electrophoresis to be 38,000.

(8) Amino Acid Composition

The enzyme of the present invention was hydrolyzed with 6M hydrochloric acid at 105° C. for 24 hours. The hydrolysate was analyzed by an amino acid analyzer (Hitachi, Model 835) to measure the amount of constituent amino acid. The measurement was repeated three times, and a ratio of the amino acid contents was calculated to obtain an amino acid composition. Results are shown in Table 3.

TABLE 3

Amino Acid Composition

| Amino Acid | Amino Acid Residue (per molecule) |
|---|---|
| Asparagine + aspartic acid | 15 |
| Threonine | 11 |
| Serine | 43 |
| Glutamine + glutamic acid | 130 |
| Glycine | 37 |
| Alanine | 17 |
| Valine | 9 |
| Methionine | 1 |
| Isoleucine | 6 |
| Leucine | 7 |
| Tyrosine | 1 |
| Phenylalanine | 4 |
| Lysine | 8 |
| Histidine | 6 |
| Arginine | 3 |
| Proline | 8 |

Note) No experiments for detection were performed for tryptophan and cystine.

As is apparent from Table 3, the amount of amino acid residue per molecule is largest in the glutamine+glutamic acid and is the second largest in serine.

Example 4

Preparation and Analysis of Lemon Low-Molecular Pectin a) Preparation of Lemon Low-Molecular Pectin (1) Preparation of Low-Molecular Pectin by JTF-1 Culture Supernatant 100 g of a lemon pectin (Wako Junyaku Kogyo) were suspended in 4 l of a 0.025 M acetic acid buffer solution (pH of 4.8), and 1 l of the culture supernatant prepared in (1) of Example 1 was added thereto. The resultant solution was reacted at 40° C. for 24 hours. The resultant reaction solution was condensed by a rotary evaporator at 60° C. and was dialyzed overnight with respect to 100-fold deionized water of the sample solution. In addition, the dialyzed product was freeze-dried to obtain 58.34 g of the lemon low-molecular pectin.

(2) Preparation of Low-Molecular Pectin by JTF-2 Culture Supernatant 59.25 g of a lemon low-molecular pectin were obtained following the same procedures as in (1) except that 1 l of the culture supernatant prepared in (2) of Example 1 was used.

(3) Preparation of Low-Molecular Pectin by JTF-3 Culture Supernatant 60.74 g of a low-molecular pectin were obtained following the same procedures as in (1) except that 1 l of the culture supernatant prepared in (3) of Example 1 was used.

(4) Preparation of Low-Molecular Pectin by JTF-4 Culture Supernatant 70.40 g of a low-molecular pectin were obtained following the same procedures as in (1) except that 1 l of the culture supernatant prepared in (4) of Example 1 was used.

b) Analysis of Lemon Low-Molecular Pectin

The lemon low-molecular pectins obtained in (1) to (4) of a) were subjected to the following measurements (1) to (4).

(1) Measurement of Molecular Weight

The main peak of each lemon low-molecular pectin was measured by HPLC analysis using a TSK-G 4000 PW gel filtration column to calculate its molecular weight using Pullulan (STANDARD P-82, Showa Denko) as the standard sample.

(2) Measurement of Ratio of Galacturonic Acid to Neutral Sugar

After each lemon low-molecular pectin was perfectly decomposed using Driselase (KYOWA HAKKO), the ratio of galacturonic acid to neutral sugar was measured by HPLC analysis using a Shodex Sugar SH-1821 column (S. Matsuhashi, S. Inoue and C. Hatanaka, Biosci. Biotech. Biochem., 56, p. 1053 (1992)). The ratio of galaturonic acid to neutral sugar was 86.3–87.7:12.4–13.7.

(3) Measurement I of Viscosity

A 5% solution of each lemon low-molecular pectin according to the present invention was prepared, and its viscosity was measured using an E type viscometer (Tokyo Keiki, VISCONIC ED Type).

Results in the above measurements (1) to (3) are shown in Table 4.

TABLE 4

| | Low-Molecular Pectin by JTF-1 Culture Supernatant | Low-Molecular Pectin by JTF-2 Culture Supernatant | Low-Molecular Pectin by JTF-3 Culture Supernatant | Low-Molecular Pectin by JTF-4 Culture Supernatant |
|---|---|---|---|---|
| Yield (%) | 58.34 | 59.25 | 60.74 | 70.40 |
| Molecular Weight | $6.6 \times 10^4$ | $6.6 \times 10^4$ | $6.6 \times 10^4$ | $6.6 \times 10^4$ |

TABLE 4-continued

|  | Low-Molecular Pectin by JTF-1 Culture Supernatant | Low-Molecular Pectin by JTF-2 Culture Supernatant | Low-Molecular Pectin by JTF-3 Culture Supernatant | Low-Molecular Pectin by JTF-4 Culture Supernatant |
|---|---|---|---|---|
| Galacturonic Acid:Neutral Sugar | 87.7:12.4 | 87.1:12.9 | 86.3:13.7 | 86.5:13.5 |
| Viscosity (cp) | 15.97 | 15.97 | 15.97 | 15.97 |
| Outer Appearance of 5% Aqueous Solution | yellowish brown | yellowish brown | yellowish brown | yellowish brown |

(4) Measurement II of Viscosity

The viscosity of the lemon low-molecular pectin obtained in (1) of a) was compared with that of a lemon pectin. The viscosities were measured using an E type viscometer (50 rpm). Results are shown in FIG. 5. The viscosity of the pectin was considerably reduced. FIG. 5 indicates that when the concentration of the low-molecular pectin is 1%, the viscosity is lowest about 0.9 cpm, and even when the concentration is 5%, the viscosity is as low as between 10 and 20 cpm. Therefore, it clearly shows that the low-molecular pectin of the present invention has a very low viscosity. Similar results were obtained for other low-molecular pectins.

(5) Defecation Improving Effect 4-week old SD male rats were fed with a commercial solid feed (oriental yeast solid feed MF) for 4 days and were divided into four groups each consisting of five rats. A feed containing the low-molecular pectin obtained in (1) of a) and components shown in Table 5, and a solid feed were supplied to each group, and the rats were fed for 9 days. The feces of the rats on the ninth day were collected. Results are shown in Table 6. The hardness of the feces by the solid feed was used as a reference. The hard feces are – (negative), and the soft feces are + (positive).

TABLE 5

| Component | Control Group (g) | Pectin Group (g) | Low-Molecular Pectin Group (g) |
|---|---|---|---|
| Casein | 22 | 22 | 22 |
| Lard | 9 | 9 | 9 |
| Corn oil | 1 | 1 | 1 |
| Mixed Salt | 3.5 | 3.5 | 3.5 |
| Mixed vitamin | 1 | 1 | 1 |
| Choline chloride | 0.2 | 0.2 | 0.2 |
| Cholesterol | 1 | 1 | 1 |
| Bile acid | 0.25 | 0.25 | 0.25 |
| Pectin[1] | — | 5 | — |
| Low-molecular pectin[1] | — | — | 5 |
| Sucrose | 63.3 | 58.3 | 58.3 |

[1]The pectin and the low-molecular pectin were prepared from a lemon pectin (Wako Junyaku Kogyo).

TABLE 6

|  | Solid Feed | Control Group | Pectin Group | Low-Molecular Pectin |
|---|---|---|---|---|
| Softening | 0 | – | + | + |

Judging from the above results, the low-molecular pectin prepared using the yeast of the present invention has a feces softening effect and was found to have a defecation improving effect.

Similar results were also obtained for other low-molecular pectins.

Example 5

Applications of Low-Molecular Pectin

Applications using the low-molecular pectin obtained in (1) of Example 4 will be described in the following a) to c).

a) 30% Apple Juice 6 parts of 5-time condensed apple juice, 10 parts of granulated sugar, 0.2 parts of DL-malic acid, 0.02 parts of sodium citrate, and 83 parts of distilled water were mixed with 1 part of the low-molecular pectin to prepare a 30% apple juice containing 1 wt % of the low-molecular pectin.

The juice containing the low-molecular pectin exhibited smooth nector-like physical properties.

b) Hard candy

A composition material (Table 7) containing 1 part of the low-molecular pectin was used to prepare an apple type hard candy.

Sugar, millet jelly, and water were mixed with each other, and the resultant mixture was heated to 110° C. The low-molecular pectin dissolved in a small amount of water was added to the above mixture and was boiled down to 147° C. Citric acid, spices, and a coloring agent were added to and mixed in the boiled-down mixture. The resultant mixture was cooled and molded. As a control, an apple type hard candy obtained by adding 1 part of a pectin was prepared and was compared with the hard candy of b). Results are summarized in Table 8 below.

TABLE 7

| Components (parts by weight) | |
|---|---|
| Sugar | 60 |
| Millet jelly | 40 |
| Apple juice (5-time condensed) | 2 |
| Water | 17.5 |
| Citric acid | 1 |
| Spices | 0.1 |
| Coloring agent | appropriate amount |
| Low-molecular pectin | 1 |

TABLE 8

|  | Outer Appearance | Taste | Total Evaluation |
|---|---|---|---|
| 1% low-molecular pectin-added candy | properly dispersed | sour-sweet; mild taste | very good |
| 1% pectin added-candy | lump of powder; not properly dispersed | too sour; strange taste | not satisfactory |

When 1 wt % of pectin was added to the candy material, the pectin formed a lump of powder and could not be properly dispersed. However, when the low-molecular pectin was added in the same amount as that of the pectin, the low-molecular pectin could be properly dispersed and facilitated the preparation of candies. In addition, the pectin-added candy was too sour and had a strange taste. However, the low-molecular pectin-added candy tasted good.

c) Bread

Bread was prepared using a composition material shown in Table 9.

2.5 parts of the low-molecular pectin were dissolved in water in advance, and this aqueous solution was mixed in the material (Table 9) except for a dry yeast. The resultant mixture was charged in a bread case of a Sanyo bread maker (SPM-B1), and the dry yeast was added thereto. The mixture was kneaded and fermented to bake the bread. As a control, bread was baked using the material composition (Table 9) from which the low-molecular pectin was omitted.

TABLE 9

| Components (part by weight) | |
|---|---|
| High protein flour | 250 |
| Sugar | 14 |
| Salt | 3.5 |
| Skim milk | 6.8 |
| Shortening | 15 |
| Dry yeast | 2.5 |
| Water | 180 |
| Low-molecular pectin | 2.5 |

The organoleptic test results are shown in Table 10. Bread containing about 0.5 wt % of the low-molecular pectin and bread of the control were almost the same, but the low-molecular pectin-added bread was softer than the control.

TABLE 10

| | Outer Appearance and Taste | Total Evaluation |
|---|---|---|
| 0.5% Low-Molecular Pectin-Added Bread | Slight yeast-like smell; softer than the control; uniformly baked in brown | good |
| Control | pleasant smell of bread; uniformly baked in brown | good |

The above tests a) to c) were also conducted for the low-molecular pectins obtained in (2) to (4) of Example 4, and similar results were obtained.

Example 6

Preparation of Apple Low-Molecular Pectin

Apple low-molecular pectins were prepared from an apple pectin (Wako Junyaku Kogyo) obtained following the same procedures as in (1) of Example 4, using the culture supernatants prepared in (1) and (3) of Example 1. Each of the resultant low-molecular pectins had a molecular weight of $6.6 \times 10^4$.

Example 7

Preparation of Low-Molecular Pectin by Culture Supernatant Obtained by Dialysis (1) Preparation of Low-Molecular Pectin Using Culture Supernatant of Crude Enzyme Solution Obtained from JTF-1

A low-molecular pectin was prepared following the same procedures as in Example 4 except that a culture supernatant obtained by dialyzing overnight 1 l of the supernatant obtained in the method of (1) of Example 1 against 300 l of a 0.025M acetic acid buffer solution (pH of 4.8) was used in place of the culture supernatant prepared in the method of (1) of Example 1. The resultant low-molecular pectin had a molecular weight of $6.6 \times 10^4$.

(2) Preparation of Low-Molecular Pectin Using Culture Supernatant of Crude Enzyme Solution Obtained from JTF-2

A low-molecular pectin was prepared following the same procedures as in Example 4 except that a culture supernatant obtained by dialyzing overnight 1 l of the supernatant obtained in the method of (2) of Example 1 against 300 l of a 0.025M acetic acid buffer solution (pH of 4.8) was used in place of the culture supernatant prepared in the method of (2) of Example 1. The resultant low-molecular pectin had a molecular weight of $6.6 \times 10^4$.

(3) Preparation of Low-Molecular Pectin Using Culture Supernatant of Crude Enzyme Solution Obtained from JTF-3

A low-molecular pectin was prepared following the same procedures as in Example 4 except that a culture supernatant obtained by dialyzing overnight 1 l of the supernatant obtained in the method of (3) of Example 1 against 300 l of a 0.025M acetic acid buffer solution (pH of 4.8) was used in place of the culture supernatant prepared in the method of (3) of Example 1. The resultant low-molecular pectin had a molecular weight of $6.6 \times 10^4$.

(4) Preparation of Low-Molecular Pectin Using Culture Supernatant of Crude Enzyme Solution Obtained from JTF-4

A low-molecular pectin was prepared following the same procedures as in Example 4 except that a culture supernatant obtained by dialyzing overnight 1 l of the supernatant obtained in the method of (4) of Example 1 against 300 l of a 0.025M acetic acid buffer solution (pH of 4.8) was used in place of the culture supernatant prepared in the method of (4) of Example 1. The resultant low-molecular pectin had a molecular weight of $6.6 \times 10^4$.

What is claimed is:

1. A purified pectinase for decomposing a pectin or pectic acid, wherein (i) said pectinase is an endopolygalacturonase produced from a *Saccharomyces bayanus*, (ii) an optimal pH upon reaction with pectic acid at 35° C. is 4.0, (iii) a stable pH range during heating at 35° C. for 60 minutes is 4.0 to 8.0, (iv) an optimal temperature upon reaction at a pH of 5.0 is 45° C., (v) an enzymatic activity upon heating at a pH of 5.0 for 60 minutes is stable up to 45° C., (vi) a molecular weight measured by polyacrylamide electrophoresis is 38,000 and, (vii) the decomposition of the pectin or pectic acid stops at a molecular weight of about 20,000.

2. The purified pectinase for decomposing a pectin or pectic acid according to claim 1, wherein the endopolygalacturonase is obtained from a strain of *Saccharomyces bayanus* having accession number FERM BP-3916.

* * * * *